(12) United States Patent
Hirota et al.

(10) Patent No.: US 6,875,402 B2
(45) Date of Patent: Apr. 5, 2005

(54) MICROPIPETTE, DISPENSER AND METHOD FOR PRODUCING BIOCHIP

(75) Inventors: Toshikazu Hirota, Nagoya (JP); Takao Ohnishi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 376 days.

(21) Appl. No.: 09/977,567

(22) Filed: Oct. 15, 2001

(65) Prior Publication Data

US 2002/0122748 A1 Sep. 5, 2002

(30) Foreign Application Priority Data

Oct. 16, 2000 (JP) ........................................ 2000-315643

(51) Int. Cl.$^7$ .............................. B01L 3/02; G01N 1/10; B05B 3/04; B05B 1/26
(52) U.S. Cl. ..................... 422/100; 422/928; 73/863.32; 73/864; 73/864.01; 73/864.12; 73/864.11; 73/DIG. 4; 239/102.2; 239/601; 436/180
(58) Field of Search ................................ 422/100, 928; 73/863.32, 864, 864.01, 864.02, 864.11, DIG. 4; 239/601, 502, 498, 102.2

(56) References Cited

U.S. PATENT DOCUMENTS

| | | | | |
|---|---|---|---|---|
| 5,370,842 A | * | 12/1994 | Miyazaki et al. | 422/82.06 |
| 5,664,733 A | * | 9/1997 | Lott | 239/429 |
| 5,925,732 A | * | 7/1999 | Ecker et al. | 530/334 |
| 6,106,685 A | * | 8/2000 | McBride et al. | 204/600 |
| 6,123,413 A | * | 9/2000 | Agarwal et al. | 347/47 |
| 6,232,129 B1 | * | 5/2001 | Wiktor | 436/180 |
| 6,296,811 B1 | * | 10/2001 | Sasaki | 422/100 |
| 6,461,812 B2 | * | 10/2002 | Barth et al. | 435/6 |
| 6,474,566 B1 | * | 11/2002 | Hirota et al. | 239/102.2 |
| 6,503,454 B1 | * | 1/2003 | Hadimioglu et al. | 422/100 |
| 6,508,411 B1 | * | 1/2003 | Ohnishi et al. | 239/4 |
| 6,533,197 B1 | * | 3/2003 | Takeuchi et al. | 239/596 |
| 6,596,239 B2 | * | 7/2003 | Williams et al. | 422/100 |
| 6,623,700 B1 | * | 9/2003 | Horine et al. | 422/100 |
| RE38,281 E | * | 10/2003 | Tisone | 422/100 |
| 6,656,432 B1 | * | 12/2003 | Hirota et al. | 422/100 |
| 6,656,740 B1 | * | 12/2003 | Caren et al. | 436/164 |
| 6,713,022 B1 | * | 3/2004 | Noolandi et al. | 422/100 |
| 6,722,582 B2 | * | 4/2004 | Hess et al. | 239/102.2 |
| 2002/0025582 A1 | * | 2/2002 | Hubbard et al. | 436/180 |
| 2002/0106812 A1 | * | 8/2002 | Fisher | 436/180 |
| 2002/0150511 A1 | * | 10/2002 | Wiktor | 422/100 |
| 2003/0143122 A1 | * | 7/2003 | Sander | 422/100 |
| 2004/0037743 A1 | * | 2/2004 | Hirota et al. | 422/68.1 |
| 2004/0082076 A1 | * | 4/2004 | Zengerle et al. | 436/180 |

FOREIGN PATENT DOCUMENTS

JP  03101960 A  4/1991

\* cited by examiner

*Primary Examiner*—Jill Warden
*Assistant Examiner*—Brian R Gordon
(74) *Attorney, Agent, or Firm*—Burr & Brown

(57) ABSTRACT

A micropipette usable for producing a biochip inclusive of DNA micro arrays capable of arraying and fixing droplets of a micro-volume on a substrate in a high density includes a main body, at least one cavity for storing a sample, at least one ejection port, a piezoelectic/electrostrictive element mounted on the outer surface of the main body, and at least one sample inlet port for supplying sample from the outside. A sample that is temporarily stored in the cavity is discharged from at least one ejection port, by virtue of the movement of the piezoelectric/electrostrictive element, to outside of the micropipette via a through hole in a nozzle portion formed in the pipette main body. The nozzle portion through hole has three or more projection radially protruding from the center of the through hole and having a specific shape.

25 Claims, 12 Drawing Sheets

MICROPIPETTE, DISPENSER AND METHOD FOR PRODUCING BIOCHIP

BACKGROUND OF THE INVENTION

1. Field of the Invention

The present invention relates to a micropipette, a dispenser and a method for producing a biochip of DNA micro arrays or the like, more specifically, to a micropipette, a dispenser in which the micropipette is used, and a method for producing a biochip which are preferably used in the field of producing a biochip of DNA micro arrays or the like, in which case a work for arranging and fixing droplets having a very small volume on a substrate with a high density, that is, a work for forming micro spots, is required, so that a high precision work for forming micro spots is feasible and thus a high quality in products to be obtained can be attained.

2. Description of the Related Art

In recent years, a great progress is found in the method for analyzing a gene structure. In fact, various gene structures including the gene of a human kind have been made clear. In the analysis of such a gene structure, a DNA micro array is used, in which several thousands to several tens of thousands of different DNA fragments are arranged and then fixed as micro spots on a substrate such as a microscopic glass slide.

As a method for forming micro spots in producing a DNA micro array, the QUILL method, the pin and ring method or the spring-pin method is normally used. In all of the methods, it is necessary to suppress deviations in the volume and shape of each micro spot and to maintain the spacing between adjacent micro spots at a fixed value, and further to avoid the contamination due to the mutual mixture of the micro spots. A requirement for further increasing the density of the micro spots, further precisely forming the micro spots in a fine arrangement, and further enhancing the quality in a product to be obtained is still increasing.

In the QUILL method, a sample is retained at a concave part in the tip of a pin, and when the tip of the pin comes into contact with a substrate, the sample at the concave part is transferred to the substrate, and therefore a micro spot is formed there. In this method, there are the following problems: The reduction in the durability of the pin due to the deformation and/or a damage resulting from the contact of the tip of the pin with the substrate; and an increase in the cross contamination of the micro spots due to the incompleteness of cleaning the sample stored at the concave part.

In the pin and ring method, a sample solution in a micro plate is reserved by a ring, and the sample inside the ring is then picked up by pin passing through the inside of the ring in which the solution is reserved, thus enabling spots to be formed on a substrate. In this method, the number of samples, which can be reserved in one process, depends on the number of rings, and the latter number is normally less than ten. Accordingly, when it is necessary to form micro spots including several thousand to several tens of thousands of kinds of samples, several hundred to several thousand processes for cleaning and drying are required. This provides a problem regarding the productivity.

In the spring-pin method, however, a sample is adhered to the tip of a pin, and when the tip of the pin comes into contact with a substrate, the sample is transferred to the substrate, so that micro spots are formed on the substrate. Moreover, a dual spring structure including springs is used to transfer the sample, reducing the damage of the pins and substrate. In this case, only one process of spotting is basically achieved by one process of reserving the samples. This also causes a problem regarding the productivity.

In these conventional methods for forming micro spots, the sample solution is transferred onto the substrate in the state of exposing it to the atmosphere. Accordingly, the sample is dried in the course of transmission, thereby making it impossible to form the spots. This causes a problem regarding the efficiency in using a very expensive sample solution.

In order to overcome the above-mentioned problems resided in the methods for producing micro spots, a non-contact spotting method can be employed. As a device for dispensing a very small amount of a biomaterial with a high precision using the method, a micropipette wherein the piezoelectric/electrostrictive element is used as a micro-pump and a dispenser in which the micropipettes used are developed and put to practical use.

In the non-contact spotting method, a biomaterial containing a nucleic acid, an amino acid or the like is ejected as micro droplets into the air and adhered to a substrate of a slide plate, so that the above-mentioned problems in the methods, where the tip of a pin is in contact with the substrate, can be overcome.

In this method, however, a biomaterial having a relatively high viscosity is ejected as micro droplets into the air and then adhered to the substrate of the slide plate. Consequently, in addition to desired droplets (desired ejected droplets), so-called satellites (spray-like droplets being smaller than the desired ejected droplets) are produced and then adhered to the substrate. This causes problems regarding the quality in the products to be obtained, for instance, the generation of spots at positions other than the aimed positions of the desired spots, the disturbance in a fixed spacing between the adjacent micro spots, the generation of contamination due to the mutual mixture of the micro spots, etc. In some cases, such satellites do not generate at the initial stage of operating the dispenser, but generate after a while. This provides a very difficult problem in the production process control.

When, moreover, the ejecting velocity of the droplets increases, the energy of the droplets increases just at the moment at which the droplets are adhered to the substrate of the slide plate, and therefore sprays (splashes) are generated. Hence, this causes a problem that undesired spots (this can also be mentioned as satellites) resulting from the splashes are generated around desired spots. A decrease in the velocity of ejecting may suppress the generation of satellites. When, however, the velocity of ejecting is decreased, there occurs a problem that the ejection becomes unstable.

In order to form spots with a high density, it is necessary to always stabilize the ejection of droplets in a constant (straight) direction. For this purpose, it is principally possible to reduce the scattering in the direction of ejection by decreasing the spacing between the substrate of the slide plate and the nozzles for ejection. However, this causes such a problem that the decrease of the spacing becomes impossible because the slide plate itself includes varied positional thickness and, adding thereto, it is impossible to avoid the increase of cost, if the mechanical accuracy of the spotting machine itself must be improved.

Moreover, the biomaterial containing, e.g., DNA or the like normally has a greater viscosity, so that, after ejection and deposition, it is necessary to quickly dry it so as not to extend the spots on the substrate of the slide plate. In the case of using such a sample, there are problems that the nozzle for ejection is prone to be dried and the nozzle is prone to be clogged due to the increased viscosity of the sample, thereby making it impossible to eject the sample therefrom.

On the other hand, the spotting method employing an ink jet method in a printer has been investigated. Such an ink jet recording head has been disclosed in, for instance, JP-A-59-178258, wherein the opening of the nozzle for ejecting the ink has at least one angular corner and the capillary force resulting from the corner is used.

Although the head disclosed in the publication has an appreciated effect of preventing the bubbles from entering the nozzle, no such a satisfactory result as mentioned above can be obtained regarding the suppression of the generation of the so-called satellites or the like.

An ink jet head having a symmetric 2n-corner polygon shape of the opening for ejecting the sample (n is an integral number greater than 3) and having an ink channel, whose cross section in the direction perpendicular to the ejecting direction is trapezoidal, has been disclosed in Japanese Unexamined Patent Application Publication No. 3-101960.

Although the head disclosed in this publication also provides a prominent effect regarding both the required amount of ink droplets and the ejecting velocity thereof, no such a satisfactory result as mentioned above can be obtained to suppress the generation of the so-called satellites or the like.

Since, moreover, the subject matter of the inventions disclosed in these publications are not mainly directed to form the spots of biomaterials, but to form the spots of an ink material, it is difficult to directly apply the techniques disclosed in these publications to the present invention. Namely, there is a serious problem from the viewpoint of the size and cost if several thousands to several tens of thousands of separate channels are disposed in such an ink jet recording head. In the ink jet method, moreover, there is a problem from the viewpoint of the efficiency in usage of the sample, since it is necessary for ink jet recording heads to fill the pumps with the sample prior to spotting without generation of bubbles, so that it is necessary to use a greater amount of samples for purge. In general, it is very effective, if a liquid can move in a channel including a pump chamber with a high speed. In the case of using a delicate DNA solution, however, there is a problem regarding the damage of the DNA or the like due to the stirring of the sample in the channels.

SUMMARY OF THE INVENTION

Taking the above-mentioned problems into account, it is an object of the present invention to provide a micropipette, which is preferably used in the field of producing a biochip including DNA micro arrays, in which case a work for arranging and fixing droplets having a very small volume on a substrate with a high density, that is a work for forming micro spots, is required, so that a high precision work for forming micro spots is feasible and thus a high quality of products to be obtained can be attained.

It is another object of the present invention to provide a dispenser, in which the above-mentioned micropipette is used, thereby making it possible to form micro spots with a high efficiency by separately ejecting several hundred to several thousand samples of different types in one operation.

It is another object of the present invention to provide a method for producing a biochip by utilizing the above-mentioned dispenser, thereby enabling the productivity to be greatly enhanced.

In accordance with the present invention, the following micropipette, the following dispenser and the following method for manufacturing a biochip can be provided in order to attain the above-mentioned objects.

The present invention is a micropipette that ejects a predetermined amount of a sample stored in a cavity from a sample ejection port by changing the volume of the cavity with the aid of the activation of a piezoelectric/ electrostrictive element mounted on an outer surface of a portion opposite to a portion, wherein the cavity is formed within a pipette main body. A sample inlet port supplies the sample from the outside of the pipette main body, with the cavity for receiving and temporarily storing the supplied sample and the sample ejection port for ejecting the stored sample to the outside via a through hole in a nozzle portion being disposed in the pipette main body. The shape of the cross section perpendicular to the direction of the axis of the through hole in the nozzle portion shows more than three projections radially protruding from the center of the through hole, thus exhibiting either a polygon having acute and obtuse interior angles or a crown shape formed by connecting the projections to each other, and the cross section area of the through hole gradually decreases from the sample supplying opening end to the sample discharging opening end, preserving a similar shape.

The present invention pertains to a micropipette that ejects a predetermined amount of a sample stored in a cavity from a sample ejection port by changing the volume of the cavity with the aid of the activation of a piezoelectric/ electrostrictive element mounted on an outer surface of a portion opposite to a portion, wherein the cavity is formed within a pipette main body. A sample inlet port supplies the sample from the outside of the pipette main body, with the cavity for receiving and temporarily storing the supplied sample and the sample ejection port for ejecting the stored sample to the outside via a through hole in a nozzle portion being disposed in the pipette main body. A shape of a cross section perpendicular to a direction of an axis of the through hole in the nozzle portion is approximately circular in the cross section from the sample supplying opening end towards the sample discharging opening end to a first position located at a predetermined length therefrom. The shape of the cross section perpendicular to the direction of the axis of the through hole shows more than three projections radially protruding from the center of the through hole, thereby exhibiting either a polygon having acute and obtuse interior angles or a crown shape formed by connecting the projections to each other at the end of the sample discharging opening, and the cross sectional area of the through hole gradually decreases from the sample supplying opening end, while retaining almost a round shape until a first point, to the sample discharging opening end.

In the micropipette according to the present invention, the angle between straight lines determined by connecting the apexes of the adjacent projections to the center either in the polygon or in the crown shape having said projections is 1 degree to 120 degrees.

In the micropipette of the present invention, the total length of the circumference of the polygon or the crown shape is more than 1.1 times larger than the length of the circumference of a circle having the same area as the cross section of the polygon or the crown shape.

In the micropipette of the present invention, the rate of continuous decreasing in the cross section area of the through hole in the nozzle portion from the sample supplying opening end to a second position located at a predetermined length therefrom towards the sample discharging opening end is greater than that from the second position to the sample discharging opening end.

In the micropipette of the present invention, the surface roughness of the inner surfaces of the through hole in the nozzle portion is greater than that of the major surface in which the sample supplying opening of the through hole is formed.

In the micropipette of the present invention, the surface in the vicinity of the sample discharging opening end of the through hole in the nozzle portion is treated by a liquid repellent.

In the micropipette of the present invention, at least at the portion where the cavity is disposed and at least at the portion where the piezoelectric/electrostrictive element is disposed, the pipette main body is made of zirconia ceramics.

In the micropipette of the present invention, the pipette main body formed from zirconia ceramics is produced by laminating and sintering green sheets.

The micropipette of the present invention can include a pipette main body formed from resin at the portion where the sample ejection port is formed.

The micropipette of the present invention includes a piezoelectric/electrostrictive element that is formed from piezoelectric/electrostrictive layers containing at least one lead compound in a group of lead zirconate, lead titanate and lead magnesium niobite as a main component.

In the micropipette according to the present invention, the pipette main body is provided with a plurality of sample inlet ports, a plurality of cavities and a plurality of sample ejection ports.

The micropipette according to the present invention includes a pipette main body that is constituted with a plurality of first pipette elements and a second pipette element, and the cavity and the piezoelectric/electrostrictive element are disposed in the first pipette elements, and a plurality of sample inlet ports and a plurality of sample ejection ports are disposed in the second pipette element. A plurality of the first pipette elements and a plurality of the second pipette elements are bonded to each other.

The micropipette according to the present invention can have a pipette main body that is formed by a flat plate product, and the sample ejection ports are disposed on the side surface or the main surface of the pipette main body.

The micropipette of the present invention can also have a pipette main body that is formed by a flat plate product, and the sample ejection ports are disposed on one main surface of the pipette main body, whereas the sample inlet port is disposed on the other main surface.

In the micropipette described above, a plurality of the sample inlet ports can be connected to the cavity.

The present invention further pertains to a micropipette composite unit formed by fixing a plurality of the above-described micropipettes to a fixing tool.

The present invention pertains to a dispenser including either a plurality of micropipettes, as described above, or more than one of a micropipette composite unit having sample ejection ports in the pipette main body are disposed in the form of matrix, and liquid samples of different kinds ejected from the sample ejection ports.

The dispenser includes a first cartridge in which liquid samples of different kinds are stored is disposed to face the sample inlet ports.

The dispenser according to the present invention can also have a second cartridge, in which an aqueous solvent or an organic solvent is stored, disposed to face the sample inlet ports, and connecting spaces formed from the sample inlet ports to the sample ejection ports of said pipette main body can be cleaned with the aqueous solvent or the organic solvent.

The dispenser according to the present invention includes a thin plate for rejecting droplets flying in a deviated direction and is disposed to face the sample ejection ports in the pipette main body. The thin plate has openings whose centers are coaxially aligned in the direction of the center axes of the sample ejection ports.

The present invention further pertains to a method for producing a biochip using the above-described micropipette, micropipette composite unit, or dispenser.

DETAILED DESCRIPTION OF THE INVENTION

Figure 1A:
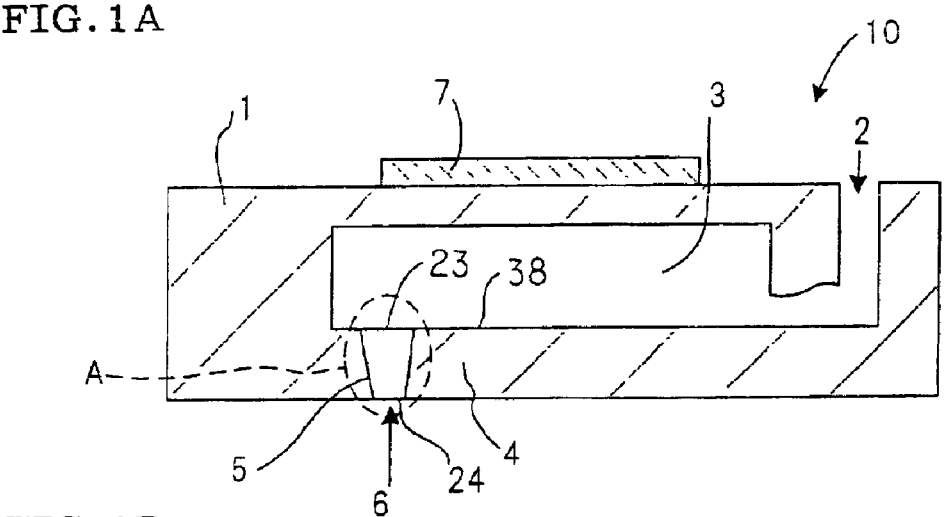
FIGS. 1A to 1C are a longitudinal sectional view, a detailed longitudinal sectional view, and a perspective view of a cavity portion, respectively, according to an embodiment of a micropipette according to the invention.

Referring now to the drawings, the preferred embodiments of the present invention are described in detail.

I. Micropipette

As shown in FIG. 1A, a micropipette 10 according to the invention comprises a pipette main body 1 having a sample inlet port 2 for supplying a sample from the outside of the pipette main body 1, a cavity 3 for receiving the supplied sample and then temporally storing the sample, and a sample ejection port 6 for ejecting the stored sample to the outside via a through hole 5 at a nozzle portion 4. A piezoelectric/electrostrictive element 7 is mounted onto the outer surface of a portion opposite to a portion, wherein the cavity 3 is formed, of the pipette main body, so that the micropipette 10 permits ejecting a predetermined amount of the sample stored in the cavity 3 from the sample ejection port 6 with the aid of the change in the volume of the cavity 3, which results from the activation of the piezoelectric/electrostrictive element 7.

Actually, the nozzle portion 4 is formed by a thin plate PET resin nozzle plate 11 in which the sample ejection port 6 including through holes 5 is disposed. In this case, the nozzle portion 4 (through holes 5) can normally be formed by machining the nozzle plate with a punch of a die assembly. When, however, the material for the nozzle portion is resin, for instance, PET, polyimide or the like, a laser beam machining (for instance, machining using an exicimer laser or higher order (more than third) YAG laser can preferably be used. The formation of a through hole for the sectional shape in the direction vertical to the axial direction can be achieved either with the so-called beam scanning method in which a laser beam is moved along the contour of the cross section of the through hole or with the so-called mask method in which a mask resembling the contour of the cross section of the through hole is formed in advance, and then the mask is positioned in the ray path of a laser beam illumination. Of these methods, the mask method is particularly suitable for simultaneously forming a plurality of through holes. On the other hand, the pipette main body 1 is constituted in such a manner that a pump part 12 is formed by both a spacer plate 14 including one or more window parts 13 and a closing plate 15 placed on one side of the spacer plate 14 for covering the window part 13, in which case, the spacer plate 14 and the closing plate 15 are made of green sheets of zirconia ceramics, and they are laminated and then sintered. The closing plate 15 has the sample inlet port 2, to which a connecting channel 17 and a supply aperture 16 are connected. Moreover, a piezoelectric/electrostrictive element consisting of a bottom electrode 20, a piezoelectric/electrostrictive layer 19 and a top electrode 18 is mounted onto the outer surface of the closing plate 15.

Figure 1B:
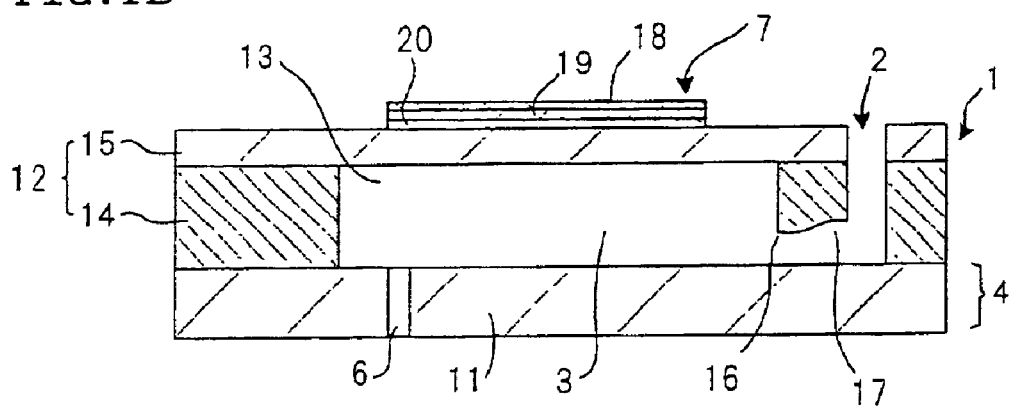

In the micropipette having such a structure, an electric field generated between the top electrode 18 and the bottom electrode 20 provides a deformation of the piezoelectric/electrostrictive element 7, so that the volume of the cavity (pressuring chamber) 3 formed by closing the window part 13 is reduced, and thus the sample (liquid including DNA fragments or the like) stored in the cavity 3 is ejected in a predetermined velocity from the sample ejection port 6 connected to the cavity 3. As a result, a biochip of DNA micro arrays which are arranged and fixed as micro spots on a substrate of a glass slide or the like can be formed. In conjunction with the above, the structure feature of a device based on the so-called ink jet method, as shown in FIGS. 1A and 1B, is disclosed in JP-A-6-40030.

In the micropipette having the above-mentioned structure, the shape and size of the channel is preferably formed in such a manner that the liquid sample including DNA fragments or the like is moved as a laminar flow in the cavity (pressurizing chamber) 3.

Figure 1C:
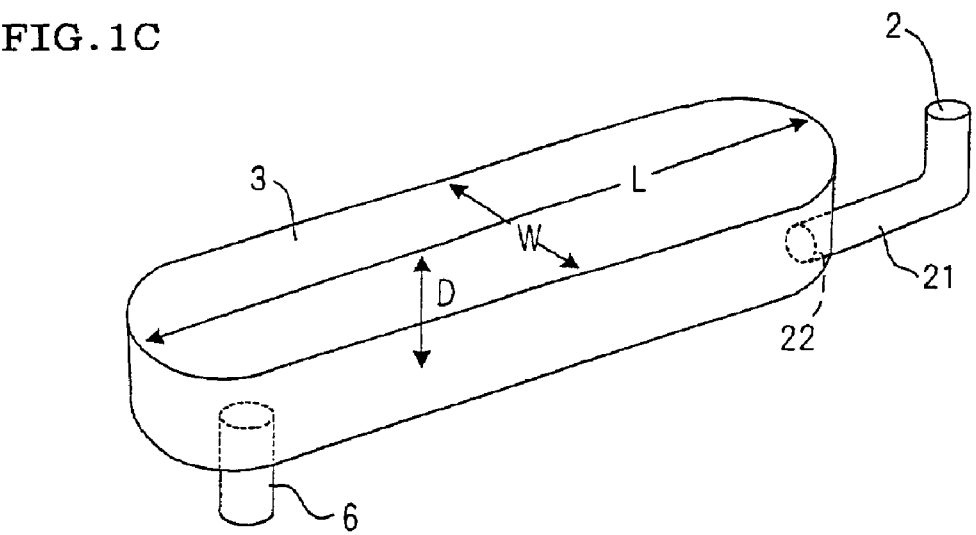

Referring now to FIG. 1C, an example of an actual cavity is described. The shape of the cavity 3 is elongated, as shown in FIG. 1C, and the elongated structure has the sample inlet port 2 or a supplying aperture 22 at one end and the sample ejection port 6 at the other end. With such a structural arrangement, the cavity 3 can be used as a part of the channel between the sample inlet port 2 and the sample ejection port 6, so that the sample moving from the sample inlet port 2 into the cavity 3 via connecting channel 21 and supplying aperture 22 is guided without disturbance from the sample inlet port 2 to the sample ejection port 6. The size of the actual cavity 3 depends on the type of sample, the size of droplets to be formed and the density of microspots to be formed. In the case of a micropipette for producing a biochip of DNA arrays or the like where droplets having a diameter of several tens to one hundred and several tens of micrometers have to be arranged with a pitch of several hundred micrometers as micro spots by preparing a sample including DNA fragments having a length of a base pair of 1 to 10000 bp dispersed in ×1TE buffer (10 mM Tris-HCl (pH 8), 1 mM EDTA) at a concentration of 0.1 to 1 $\mu g/\mu l$, it is preferable that the cavity length (L) is 1 to 5 mm,. the cavity width (W) is 0.1 to 1 mm and the cavity depth (D) is 0.1 to 0.5 mm. Moreover, the inner walls of the cavity should be smooth and should have no projections which disturb the flow of liquid. It is preferable that the material for the inner walls should be a ceramics having a good affinity to water.

By employing the above-mentioned structural arrangement according to the invention, a micro liquid is ejected from the sample ejection port in response to the activation of individual piezoelectric/electrostrictive elements, and the volume of the ejected liquid can be extremely small and can be maintained in a constant value without any disturbance. The frequency of activation can extend to a high frequency range using piezoelectric/electrostrictive elements, and can also decrease the time period necessary for ejection. Since the sample moves in a closed space until it is ejected after supplying the sample, it no longer dries in the flow channel. The pipette main body itself can be formed in a very small and compact structure, and therefore the channel in which the sample is moved can be shortened, thereby enabling the reduction of the efficiency in usage of the sample due to the adhesion of the sample onto the flow channel walls to be eliminated.

In the micropipette according to the invention, a substitution solution, such as a buffer solution, a physiological saline solution or the like is stored in advance in the cavity, and then a sample is supplied from supplying aperture into the cavity by substituting the sample for the substitution solution. After that, the sample in the cavity can be ejected from the sample ejection port by activating the piezoelectric/electrostrictive elements. The end point of completing the substitution can be controlled by the substitution time, which is determined in advance from the moving velocity and the volume of the sample. However, it is preferable that the time for substitution is determined by sensing the change of the fluid characteristics in the cavity. In another way, the sample is supplied from the sample supplying aperture into the cavity by activating the piezoelectric/electrostrictive elements, and thus can be substituted in a laminar flow. After completely supplying an inexpensive substitution solution into the cavity, an expensive sample solution is substituted for the substitution solution in a laminar flow, thereby enabling the failure of ejection to be completely suppressed and therefore enabling the expensive sample to be ejected with a high efficiency in usage.

Furthermore, in the micropipette according to the invention, a substitution solution, such as a buffer solution, a physiological saline solution or the like, is stored in advance in the cavity, and then a sample is supplied into the cavity by substituting the sample for the substitution solution, and it is preferable that after the end point of completing the substitution is determined by sensing the change of the fluid characteristics in the cavity, the sample in the cavity is ejected from the sample ejection port by activating the piezoelectric/electrostrictive elements. The determination of completing the substitution by sensing the change of the fluid characteristics in the cavity provides to easily and accurately distinguish the mixture of the sample and the substitution solution from the solution without mixture in the cavity, and therefore the amount of the sample to be purged by mixing the sample solution with the substitution solution can be reduced, thereby enabling the efficiency in usage of the sample to be enhanced.

Moreover, it is preferable that the change of the fluid characteristics in the cavity can be determined by sensing electrical constants relating to the vibration, which is induced by applying a voltage to the piezoelectric/electrostrictive elements. This procedure requires no disposition of special sensing elements and ensures a highly accurate and low cost detection.

Figure 2:
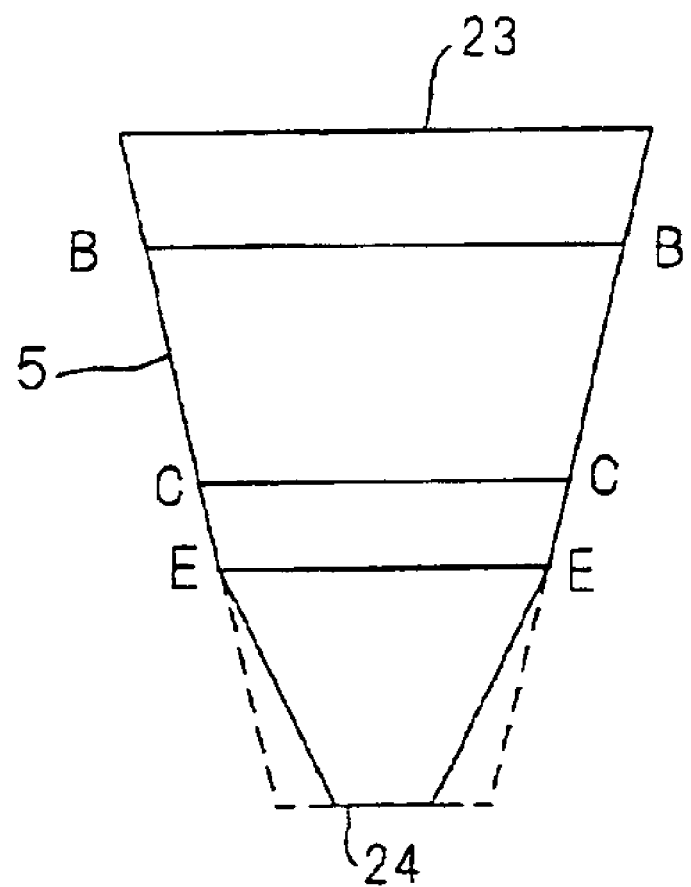
FIG. 2 is a magnified sectional view of area A in FIG. 1A.

As shown in FIG. 2, the through hole 5 in the micropipette according to the invention is constituted in such a manner that its sectional area vertical to the axial direction (cross section) gradually decreases from the sample supplying opening end 23 to the sample discharging opening end 24, while maintaining an approximately similar figure. In other words, the cross section at the sample supplying opening end 23 gradually decreases via, e.g., the cross section at line B—B and the cross section at line C—C, down to the cross section at the sample discharging opening end 24, as shown in FIG. 2.

With this structural arrangement, the disturbed flow of the sample at the sample supplying opening end 23 (the flow velocities of the sample at varied positions of the cross section being different from each other) can be homogenized till the sample arrives at the sample discharging opening end 24, so that the direction of ejection can be stabilized and therefore the flow velocity of the sample at the sample discharging opening end 24 can be effectively enhanced, and further the margin of droplets becomes more clear-cut in the case of ejection, hence enabling the generation of the so-called satellites to be suppressed.

Figure 3A:
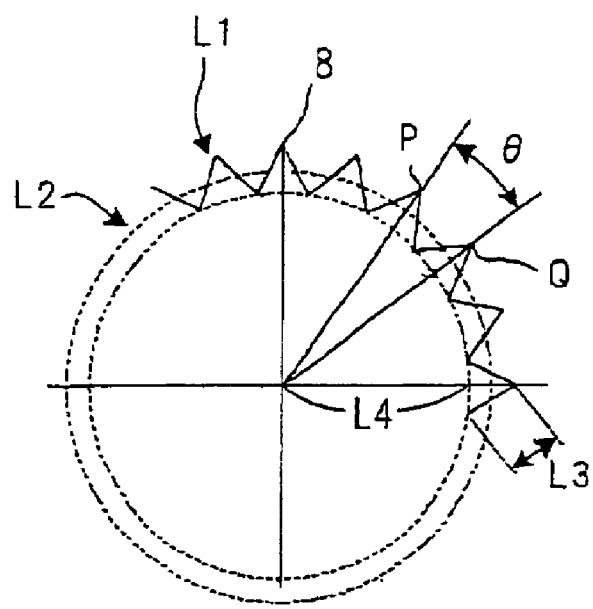
FIGS. 3A and 3B schematically show cross sections of a through hole at a nozzle portion in the micropipette according to the invention, viewed from line B—B in FIG. 2, in the case of polygon and in the case of crown shape, respectively.
Figure 3B:
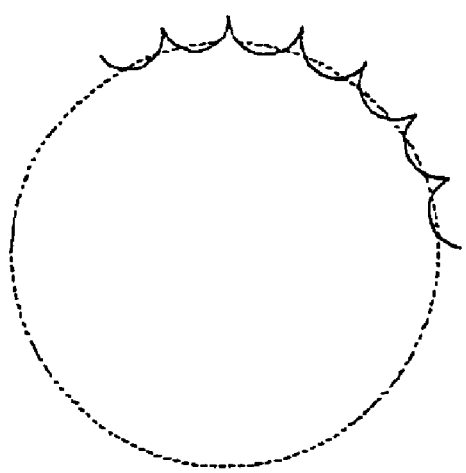
Figure 4:
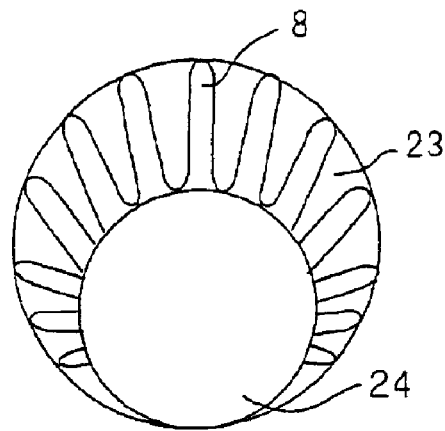
FIG. 4 is a perspective view showing projections of a through hole at the nozzle portion in an embodiment of a micropipette according to the invention.

As shown in FIGS. 3A and 3B and in FIG. 4, the cross section of the through hole 5 vertical to the axial direction (e.g., cross section viewed from line B—B in FIG. 2) is constituted in such a manner that the through hole has more than three projections 8 which radially protrude from center O, exhibiting either a polygon shape having acute and obtuse interior angles or a crown shape determined by connecting each projection to the adjacent projection.

With this structural arrangement, droplet ejected from the sample discharging opening end 24 to the outside exhibits a shape having the projections corresponding to the shape of the through hole 5 just after the ejection, and rapidly changes into a ball shape due to the surface tension, so that the sharpness in the margin of a droplet ejected from the through hole 5 increases due to the action of surface tension (a droplet is quickly formed), and the generation of the so-called satellites due to the fracture of the droplet, and a fine separation at the rear side of the droplet can be suppressed.

In addition, since the flow of the sample is regulated by the projections 8, the direction of ejection can be stabilized.

Moreover, the gradually decreased cross section area of the through hole 5 and the design thereof into a predetermined shape, which are effective both for enhancing the stabilization of the direction of ejection and for suppressing the generation of the satellites, can be effectively carried out independently of each other, but if they are simultaneously carried out, a more prominent effect can be obtained.

The polygon shape or crown shape of the projections shown in FIGS. 3A and 3B should not always be those having acute angles, but the shape having obtuse angles can be employed, depending on the material of the nozzle portion, the machining method and the accuracy of machining in a cutting machine.

Figure 5A:
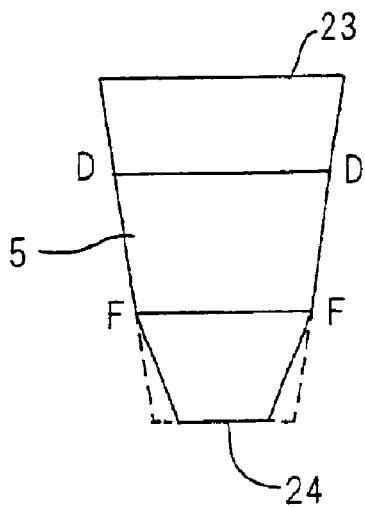
FIGS. 5A and 5B are sectional views schematically showing a through hole at the nozzle portion in another embodiment of a micropipette according to the invention, in the case of the first position being different from the second position and in the case of the first position being the same as the second position, respectively.
Figure 5B:
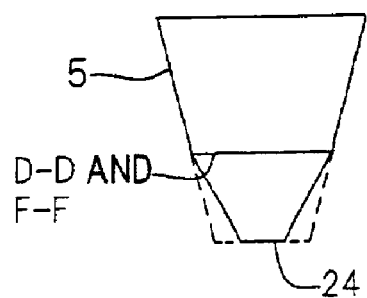
Figure 6:
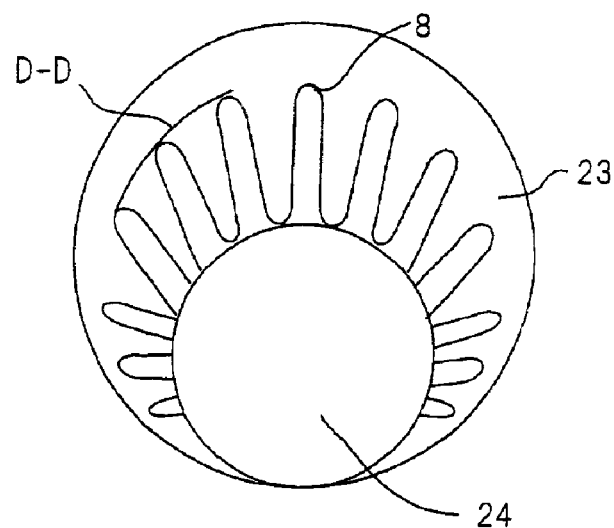
FIG. 6 is a perspective view schematically showing the projections of a through hole at the nozzle portion in another embodiment of a micropipette according to the invention.

As shown in FIGS. 5A and 5B and in FIG. 6, the micropipette according to the invention can be constituted in such a manner that the shape of the cross section of the through hole 5 vertical to the axial direction in the nozzle portion has an approximately circular shape till the first position (corresponding to line D—D in FIG. 5) located from the sample supplying opening end 23 towards the sample discharging opening end 24 at a predetermined distance and it has more than three projections 8 radially protruding from the center in an area from the first position (line D—D) to the sample discharging opening end 24, exhibiting either a polygon shape having acute and obtuse interior angles (see FIGS. 3A and 3B), and that the area of the section (the area of the cross section) gradually decreases from the sample supplying opening end 23 of the through hole to the first position (line D—D), while maintaining an approximately circular shape, and further continuously decreases till the sample discharging opening end 24. Regarding the range of the first position, it is preferable that the first position situates at an intermediate location between the sample supplying opening end 23 and the sample discharging opening end 24, i.e., if the distance between the sample supplying opening end 23 and the sample discharging opening end 24 is assumed to be 1, the first position situates at a distance of 0.1 to 0.7 from the sample supplying opening end 23. If it is less than 0.1, the cross section of the sample supplying opening end 23 (circle) cannot be stably formed, whereas if it is beyond 0.7, the homogenizing effect due to the shape of the projections becomes insufficient.

With this structural arrangement, as described above, since the margin of a droplet ejected from the through hole of the nozzle portion becomes clear-cut, resulting from the shape of the projections at the sample discharging opening end 24 (a droplet is rapidly generated), the generation of the so-called satellites, which is caused due to the fine fracture of the droplet at the rear portion of the droplet, can be suppressed. In addition, by the approximately circular shape of the sample supplying opening end 23, the pressure and flow of the sample from the cavity are uniformly transmitted to the nozzle portion, and additionally the direction of ejecting sample can be stabilized, by the effect of the homogenized flow due to the shape of the projections from the first position to the sample discharging opening end 24.

In the micropipette according to the invention, moreover, it is preferable that, as shown in FIG. 3A, the angles θ between straight lines determined by connecting the apices of adjacent projections 8 (for example, P and Q) of a polygon having projections to the center O ranges from 1 degree to 120 degrees, and it is more preferable that the angle ranges from 3 degrees to 72 degrees. If the angle is less than 1 degree, the polygon tends to a circle, thereby making it impossible to attain the effect according to the invention. If, moreover, the angle is beyond 120 degrees, the direction of ejecting the sample becomes unstable.

In the micropipette according to the invention, moreover, it is preferable that, as shown in FIG. 3, the total length L1 of the circumference of either a polygon shape or a crown shape having projections 8 is more than 1.1 times greater than the length L2 of the circumference of a circle having the same area as the polygon (L1/L2≧1.1). It is more preferable that L1 is more than 1.15 times greater than L2. If L1 is less than 1.1 times L2, the polygon shape tends to a circle, so that there is a possible generation of the so-called satellites, and the sample is dried in the vicinity of the sample discharging opening end 24, thereby inducing a failure of ejection and a possible deflection of the ejecting direction.

In the micropipette according to the invention, moreover, it is preferable that, as shown in FIG. 2 and in FIGS. 5A and 5B, the rate of the gradual decrease for the cross section area of the through hole 5 at the nozzle portion in the interval from the second position (line E—E and line F—F) to the sample discharging opening end 24 is greater than that in the interval from the sample supplying opening end 23 of the through hole to the second position (line E—E and line F—F) which is located at a predetermined distance from the sample supplying opening end 23 towards the sample discharging opening end 24. Such a two-stage decrease for the cross section area towards the sample discharging opening end 24 further enhances the effect of homogenizing the flow of sample, and also enhances the efficiency of the increase in the flow of sample at the sample discharging opening end 24. In this case, it is preferable that the range of the second position situates at an intermediate position between the sample supplying opening end 23 and the sample discharging opening end 24, in other words, if it is assumed that the distance between the sample supplying opening end 23 and the sample discharging opening end 24 is 1, the range of the second position situates at the distance of 0.3 to 0.7. If the second position coincides with the first position, as shown in FIG. 5B, this situation is favorable for suppressing the generation of the satellites and for homogenizing the sample flow, and at the same time, the through hole including both the sample supplying opening end 23 and the sample discharging opening end 24 can easily be machined. In the case of using resin such as PET, polyimide or the like as a material for the nozzle member, a laser beam machining (for instance, excimer laser, higher order (more than the third order) YAG laser can preferably be employed. Such a gradual decrease in the rate of the cross section area can be achieved by appropriately changing the power of the laser in the course of machining. In the case where the rate of decreasing of the cross section area at the interval between the sample supplying opening end 23 and the second position is smaller than that at the interval between the second position and the sample discharging opening end 24, as shown in FIG. 2 and in FIGS. 5A and 5B, the laser beam illumination is carried out at the sample supplying opening end 23, and the power of the laser can be reduced at intermediate positions.

Figure 7:
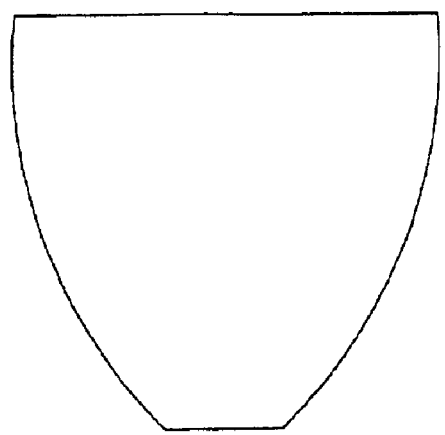
FIG. 7 is a sectional view schematically showing a gradually decreasing cross section area of a through hole at a nozzle portion.

Regarding the axial section of a through hole whose cross section area gradually decreases, a spindle-like shape of the through hole which increases the rate of the gradual decrease in the cross section area towards the sample discharging opening end 24, as shown in FIG. 7, can be employed. In this case, a machining method, in which the laser beam illumination is carried out at, for instance, the sample supplying opening end 23, and then the power of the laser gradually decreases, can be employed.

In the micropipette according to the invention, moreover, it is preferable that, as shown in FIG. 1, the surface roughness of the inner surface of the through hole 5 in the nozzle portion is greater than that of surface 38 in which the sample supplying opening end 23 of the through hole 5 is disposed. A greater surface roughness of the inner surface of the through hole relative to the other parts provides a rapid attenuation or cessation of the shaking (vibration) of the liquid surface of the sample remained in the through hole 5 after ejecting, thereby enabling the generation of satellites due to the remaining liquid to be suppressed.

In the micropipette according to the invention, moreover, it is preferable that a liquid repellent treatment is carried out for the surface in the vicinity of the sample discharging opening end of the through hole in the nozzle portion. An increase repellency of liquid for the surface in the vicinity of the sample discharging opening end further enhances the suppression of the blurring at the margin of a droplet, together with the effect due to the other structural arrangements.

In the micropipette according to the invention, moreover, it is preferable that the pipette main body is constituted by a zirconia ceramics at least at the portions at which the cavity is formed and at which the piezoelectric/electrostrictive elements are disposed. It is more preferable that all the portions of the pipette main body are made of the zirconia ceramics. In this case, the zirconia ceramics is preferably produced, using the method for laminating and then sintering green sheets. Zirconia, in particular stabilized zirconia and partially stabilized zirconia, has a greater mechanical strength, even if it is processed into a thin plate, and it has a higher toughness, an excellent stability against the acid/alkali solution and a reduced chemical reaction to the piezoelectric layer and the electrode material, so that it is excellent for the material of the pipette main body according to the invention.

Moreover, the pipette main body can be constituted by a resin at the position of the sample ejection port, taking into account the ease in molding and the manufacturing cost.

In the micropipette according to the invention, moreover, it is preferable that the piezoelectric/electrostrictive elements according to the invention is formed by piezoelectric/electrostrictive layers containing at least one lead compound among lead zironate, lead titanate and lead magnesium niobate as a main component, since such piezoelectric/electrostrictive layers have a greater electromechanical coupling coefficient, a greater piezoelectric constant and a reduced chemical reaction with the pipette main body (zirconia ceramics) in the course of sintering the piezoelectric/electrostrictive layers, thereby enabling the layers having stable components to be obtained.

Figure 8B:
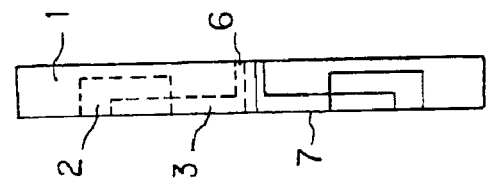
FIGS. 8A and 8B are a plan view and a sectional view from line G—G of 8A, respectively, and show another embodiment of a micropipette according to the invention schematically.
Figure 8A:
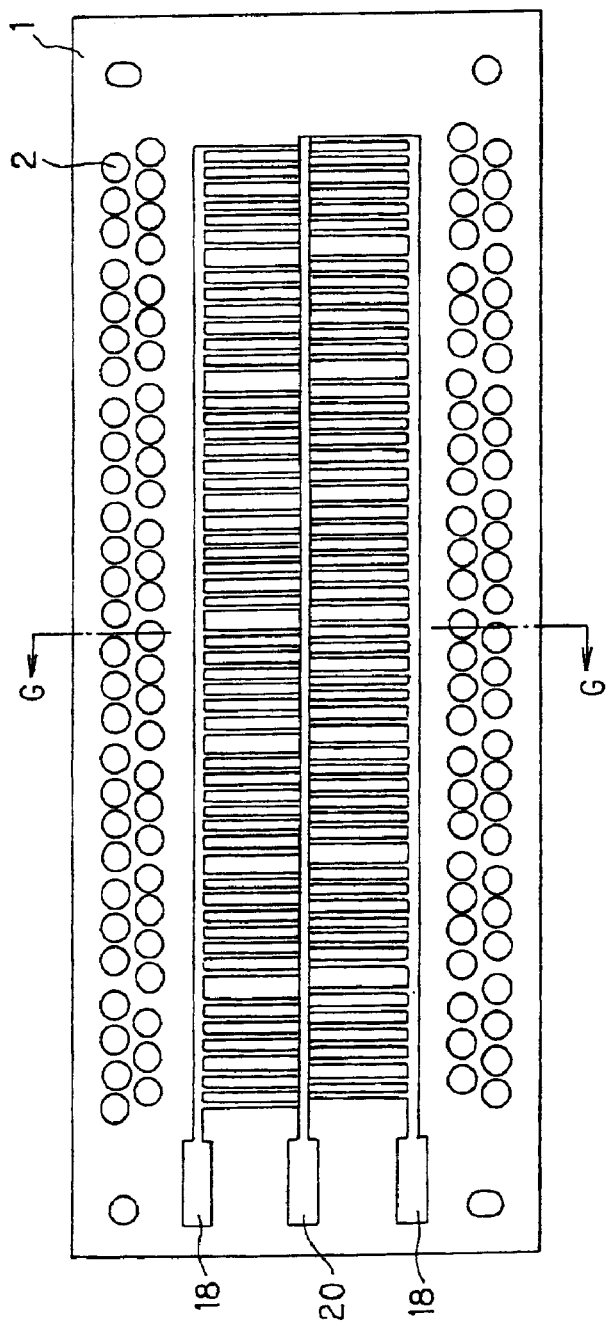

In the micropipette according to the invention, moreover, a plurality of sample inlet ports 2, a plurality of cavities 3, a plurality of sample ejection ports 6 and a plurality of piezoelectric/electrostrictive elements 7 can be disposed in a pipette main body 1, and upper electrodes 18 and lower electrodes 20 of the piezoelectric/electrostrictive elements 7 are wired at one portion, as shown in FIG. 8A. This structural arrangement ensures the formation of a compact micropipette and an accurate disposition of the sample ejection ports in a high density. In addition, various kinds of samples can be simultaneously discharged, thereby enabling the biochips such as DNA micro arrays to be manufactured with a high efficiency and a good producibility.

Figure 12A:
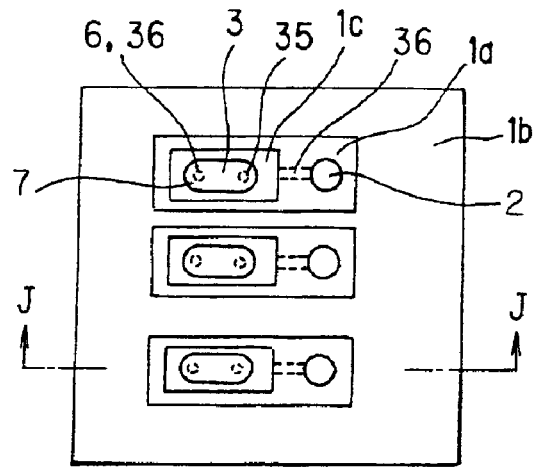
FIGS. 12A and 12B are a plan view and a sectional view from line J—J of 12A, respectively, and show another embodiment of a micropipette according to the invention schematically.
Figure 12B:
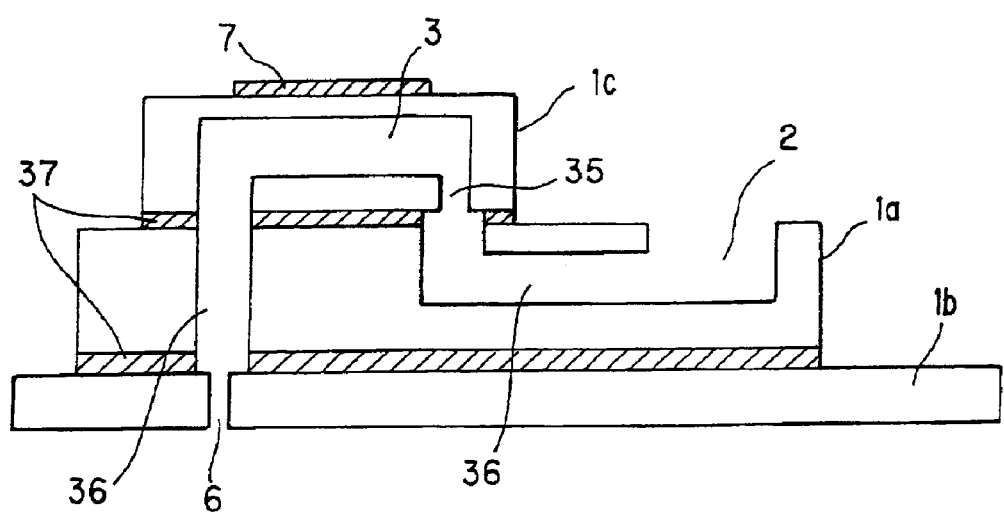

Moreover, the micropipette according to the invention can be obtained by fixing and unifying more than one of composite unit which is/are formed by joining more than one of first pipette elements in which a cavity and piezoelectric/electrostrictive element are formed to second pipette elements in which at least more than one of the sample inlet ports or the sample ejection ports is/are formed. In an actual structural arrangement, as shown in FIGS. 12A and 12B, a first pipette element 1c in which a cavity 3, a piezoelectric/electrostrictive element 7 and a supplying aperture 35 are disposed, a second pipette element 1a in which a sample inlet port 2 and two connecting channels 36 are disposed, and a third pipette element 1b in which a plurality of sample ejection ports 6 is disposed are all formed in a separate manner, in which case the second and third pipette elements correspond to the above-mentioned second pipette element, and then these pipette elements 1c, 1a and 1b are bonded to each other with a bonding agent 37.

As the materials for the first pipette element 1c, the second pipette element 1a and the third pipette element 1b, for instance, a partially stabilized zirconia, a partially stabilized zirconia and a PET resin can be employed respectively. The bonding of these pipette elements can be carried out using a mechanical method, but the bonding using a bonding agent and/or thermal diffusion method is preferable regarding the sealing property of the fluid channels.

This arrangement ensures the expansion in the extent of materials selectable for the pipette main body, so that an optimal material can be used for each portion thereof, thereby enabling the yield of the elements to be enhanced, and at the same time making it possible to accurately dispose the sample ejection ports in a high density, along with the simultaneous ejection of different kinds of samples.

Figure 9A:
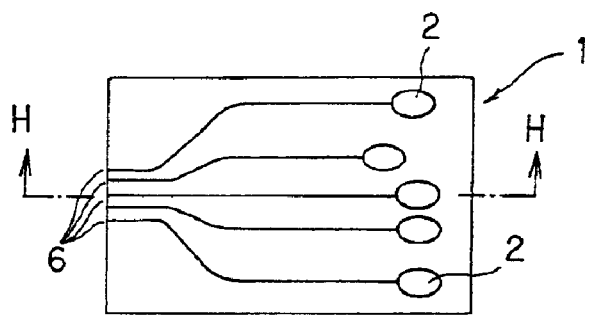
FIGS. 9A and 9B are a plan view and a sectional view from line H—H of 9A, respectively, and show another embodiment of a micropipette according to the invention schematically.
Figure 9B:
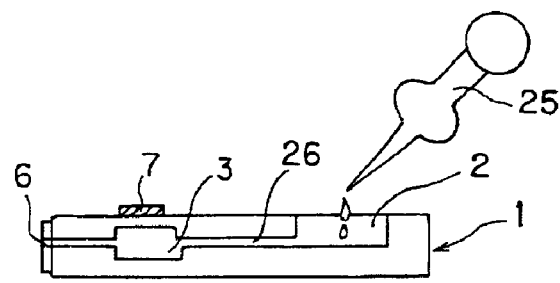

As shown in FIGS. 9A and 9B, the micropipette of the so-called edge type can be adopted in accordance with the present invention. In this case, a plurality of sample inlet ports 2, a plurality of cavities 3, a plurality of sample ejection ports 6 and a plurality of piezoelectric/electrostrictive elements 7 can be disposed in a pipette main body 1. In this micropipette, the sample ejection ports 6 are disposed on one side surface of the pipette main body 1. The sample, which is injected into one of the sample inlet ports 2 by an ordinary pipette 25, is transferred into the corresponding cavity 3 via a connecting channel 26 of the pipette main body 1. The sample thus stored in the cavity 3 can be ejected in a predetermined amount from the sample ejection port 6 by the change in the volume of the cavity 3, when the piezoelectric/electrostrictive elements 7 are activated. The arrangement of the sample ejection ports 6 on the side surface of the pipette main body 1 makes it possible to enhance the density of the sample ejection ports 6 when the flat pipette main body 1 is disposed longitudinally.

Figure 10A:
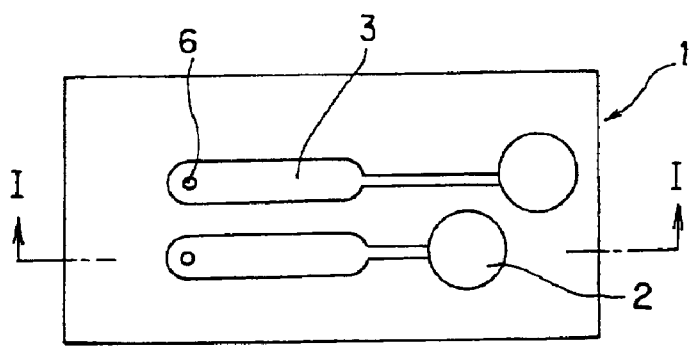
FIGS. 10A and 10B are a plan view and a sectional view from line I—I of 10A, respectively, and show another embodiment of a micropipette according to the invention schematically.
Figure 10B:
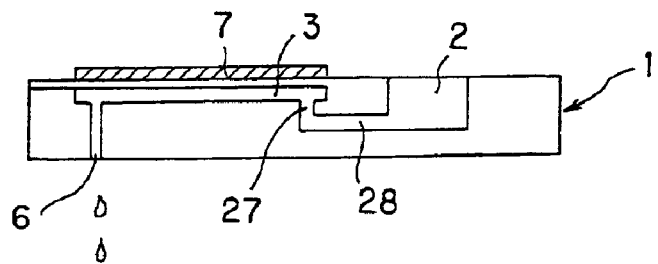

As shown in FIGS. 10A and 10B, a micropipette according to the invention is of the so-called face type, as similar to those in FIGS. 8A and 8B, in FIGS. 11A to 11D, and in FIGS. 12A and 12B, and the micropipette can be formed in such a manner that sample inlet ports 2, cavities 3, sample ejection ports 6 and piezoelectric/electrostrictive elements 7 are disposed in a pipette main body 1, as similar to that in FIGS. 9A and 9B. In this micropipette, the sample ejection ports 6 are disposed on one main surface of the pipette main body 1. A supply aperture 27 and a connecting channel 28 are connected between each cavity 3 and a corresponding sample inlet port 2, and the sample inlet port 2 is disposed on the other main surface. This structural arrangement ensures an accurate disposition of the sample ejection ports, compared with the micropipette of the edge type. The disposition of the sample ejection ports 6 on one main surface of the pipette main body 1 makes it possible to set a substrate parallel to a flat plate in which the sample ejection ports 6 are disposed, thereby enabling the droplets to be ejected in a constant distance with ease and thus allowing to stabilize the shape of the droplets. The disposition of the sample inlet port 2 and the sample ejection ports 6 in the different main surfaces ensures to approximately coincide the length of the fluid channel between the sample inlet port 2 and the sample ejection port 6 with the thickness of the flat plate, thereby providing a simple and short fluid channel. This prevents bubbles from remaining in the fluid channel and reduces the frequency of failures in the ejection, thereby enabling the efficiency in using the samples to be further enhanced.

Figure 13A:
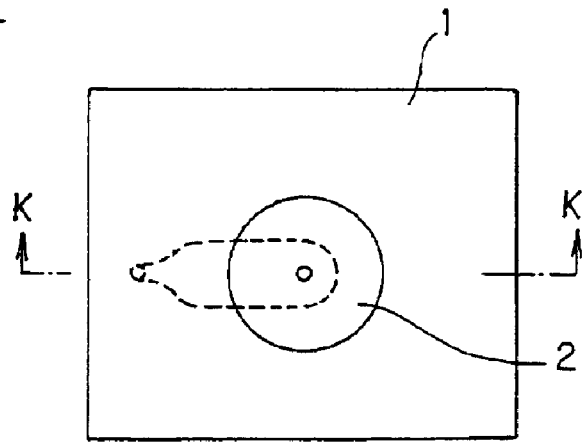
FIGS. 13A and 13B are a plan view and a sectional view from line K—K of 13A, respectively, and show another embodiment of a micropipette according to the invention schematically.
Figure 13B:
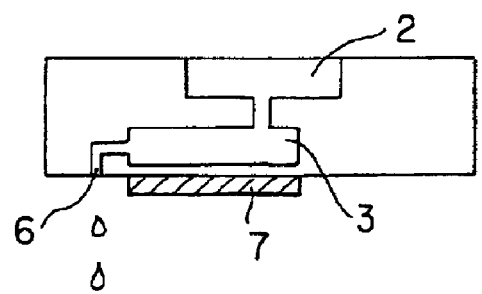

In the micropipette according to the invention, moreover, the pipette main body comprises a flat product, and the sample ejection ports are disposed either on the side walls or on the main surfaces of the pipette main body. This structural arrangement (that is, the pipette main body being flat) ensures the manufacture of the pipette main body by laminating green sheets or the like, as will be later described, thereby allowing to form a thin and compact structure of the total system. Furthermore, as shown in FIGS. 13A and 13B, the sample ejection ports 6 and the sample inlet ports 2 can be disposed on one main surface and the other main surface of the pipette main body 1, respectively, and the piezoelectric/electrostrictive elements 7 can also be disposed on the main surface similar to that for the sample ejection ports 6. In this case, any elements other than the sample inlet ports 2 are not disposed on the surface for the sample inlet ports 2, so that the supply of samples can be easily carried out.

Moreover, the micropipette according to the invention can be constituted by fixing a plurality of the abovementioned micropipettes fixed to a fixing tool, thus forming a composite unit of micropipettes.

Figure 11C:
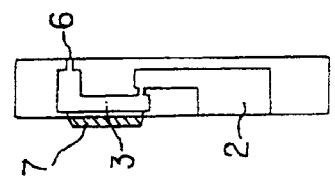
FIGS. 11A to 11D are a plan view, a side view, a magnified plan view of individual part of a composite unit, and a sectional view thereof, respectively, and show another embodiment of a micropipette according to the invention schematically.
Figure 11D:
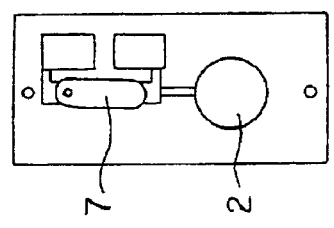
Figure 11A:
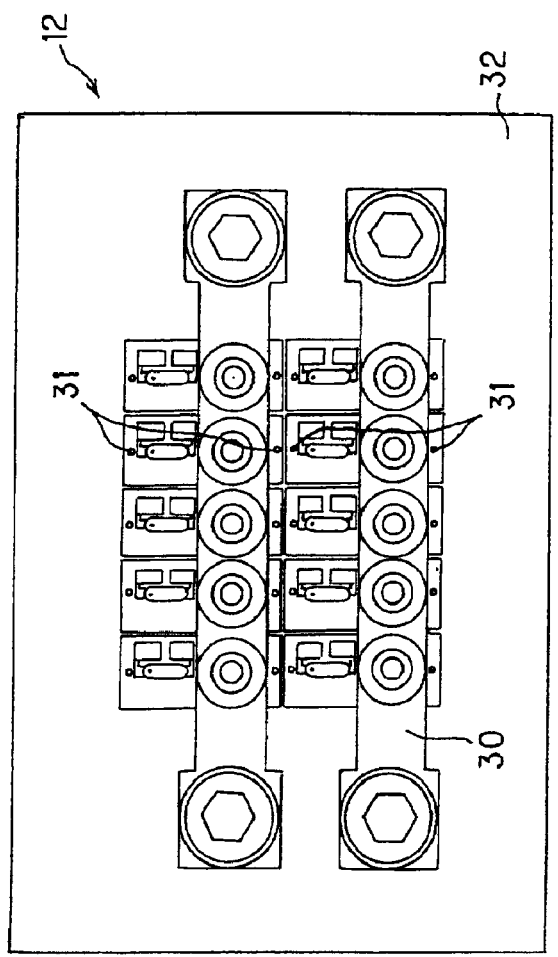
Figure 11B:
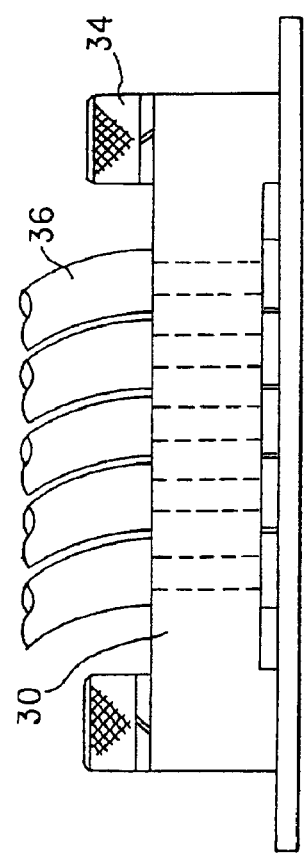

For instance, as shown in FIGS. 11A to 11D, a plurality of units, in which the sample inlet port 2, the cavity 3, the sample ejection port 6 and the piezoelectric/electrostrictive element 7 are disposed in the pipette main body 1 (see FIGS. 11C and 11D), are fixed to a fixing tool set (corresponding to the set of the belowmentioned press tools 30, positioning pins 31 and fixing plate 32). Each unit is fixed to a fixing plate 32 with the aid of the press tools 30 and the positioning pins 31 for holding tubes (connecting channels) 36 of supplying the sample to the sample inlet ports 2. In FIGS. 11A and 11B, the fixing is carried out by clamping both sides of the press tools 30 to the fixing plate 32 with screws 34. The fixing can also be carried out either mechanically with screws, springs or the like or with a bonding agent or the like.

Such a structural arrangement ensures an easy production of individual pipette main bodies, thereby enabling the yield to be enhanced.

Figure 14A:
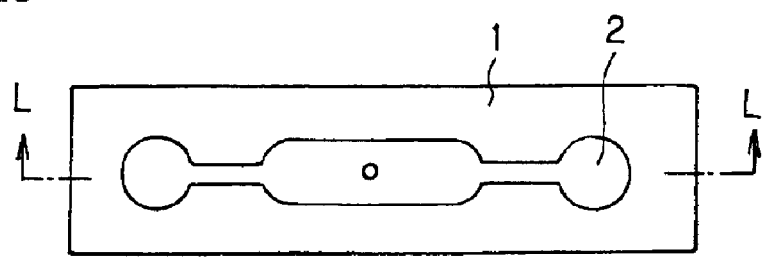
FIGS. 14A and 14B are a plan view and a sectional view from line L—L of 14A, respectively, and show another embodiment of a micropipette according to the invention schematically.
Figure 14B:
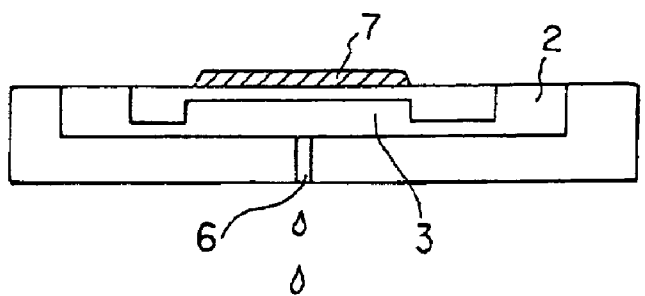

Furthermore, a composite unit of the micropipettes according to the invention can be constituted by connecting a plurality of sample inlet ports to a cavity. As shown in FIGS. 14A and 14B, there is an embodiment of an unit in which two sample inlet ports 2 are connected to a cavity 3. In this embodiment, a piezoelectric/electrostrictive element 7 is disposed on the same main surface as that for the sample inlet ports 2, whereas the sample ejection port 6 is disposed on the other main surface.

Such a structural arrangement ensures a reliable transmission of the sample or the substitution solution into the cavity, adjusting the timing, by an action of suction and/or injection.

II. Dispenser

A dispenser according to the invention comprises either a plurality of the above-mentioned micropipettes or more than one of the above-mentioned composite unit of the micropipettes, wherein sample ejection ports on a pipette main body are disposed in the form of matrix on a pipette main body, and liquid samples of different kinds can be ejected from the sample ejection ports.

Such a structural arrangement ensures to simultaneously supply a greater number of samples of different kinds and an easy exchange of damaged or deficient pipettes. Moreover, the arrangement of the sample ejection ports in the form of matrix preferably provides a two dimensional arrangement of fixed micro spots necessary for preparing the biochips such as DNA micro arrays.

Figure 15:
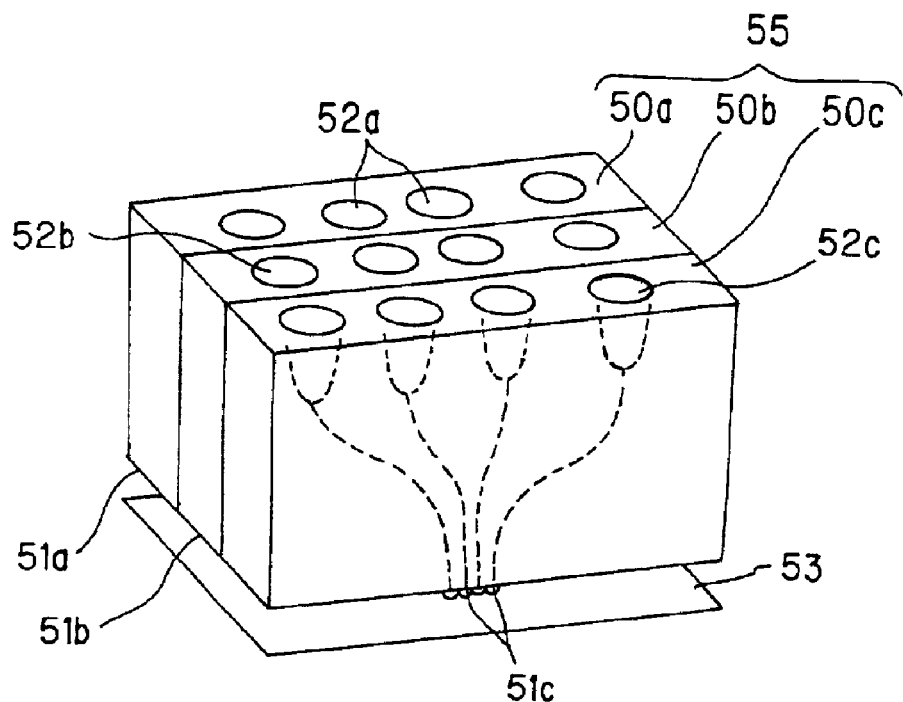
FIG. 15 is a perspective view schematically showing an embodiment of a dispenser.
Figure 16A:
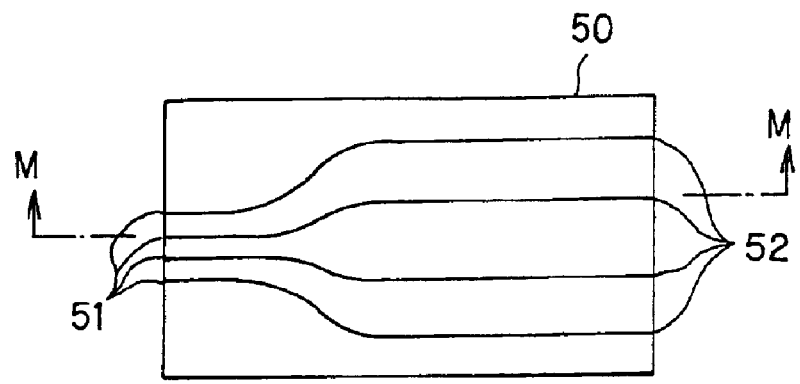
FIGS. 16A and 16B are a plan view and a sectional view from line M—M of 16A, respectively, and show the micropipette used in the dispenser of FIG. 15 schematically.
Figure 16B:
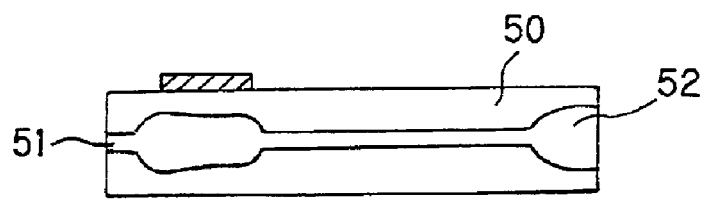

As shown in FIG. 15, a dispenser according to the invention is constituted by arranging a plurality of micropipettes 50a, 50b and 50c whose sample ejection ports are aligned in the down direction, wherein each of the micropipettes is the same as a micropipette 50 having sample inlet ports 52 and sample ejection ports 51, as shown in FIGS. 16A and 16B. Namely, in each micropipette 50a, 50b or 50c, sample inlet ports 52a, 52b or 52c are aligned in the upper direction and sample ejection ports 51a, 51b or 51c are aligned in the down direction and arranged in the form of matrix, so that the respective samples of different kinds can be ejected from the corresponding sample ejection ports 51a, 51b and 51c. In another structural arrangement, a thin plate 53 for intercepting droplets flying in the deflected direction can be disposed so as to face the pipette main body in a predetermined spacing on the side of the sample ejection ports 51a, 51b and 51c, in which case, the plate 53 has apertures whose axes are coaxially aligned in the same direction as the center axes of the sample ejection ports 51a, 51b and 51c. The structural arrangement including the plate 53 for intercepting droplets flying in the deflected direction prevents droplets from arriving at a substrate, even if the droplets are ejected in deflected directions, thereby enabling the deficiency due to the positional shift of spots and the mixture of the adjacent spots to be suppressed.

Figure 17:
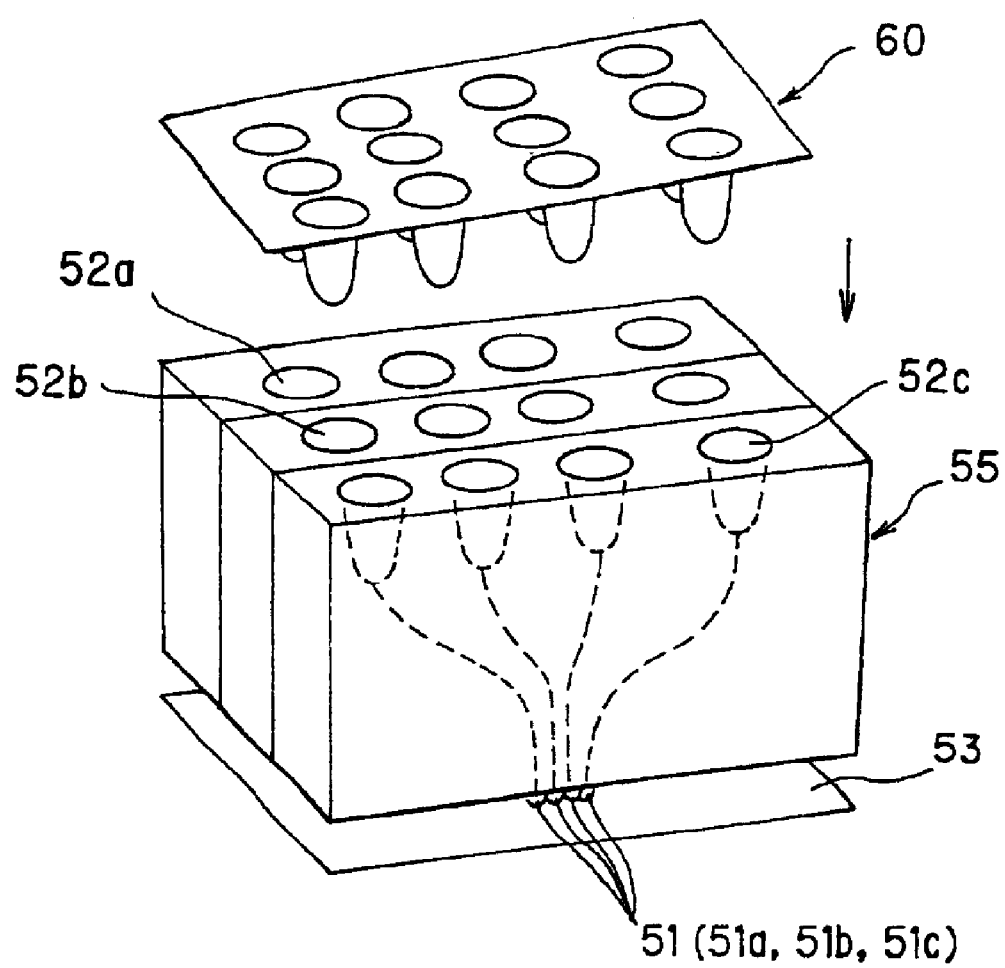
FIG. 17 is a perspective view of the dispenser to which a cartridge is adapted.

In the dispenser, as shown in FIG. 17, a first cartridge 60 in which samples of different kinds can be stored corresponding to sample inlet ports 52a,52b and 52c, is disposed, and then the samples of different kinds can be ejected from sample ejection ports 51a, 51b and 51c,thereby enabling the efficiency in the usage of these samples to be enhanced.

In addition, a second cartridge in which aqueous solvents (for instance, physiological saline solutions) or organic solvents are stored, corresponding to sample inlet ports, can be employed, and thus it is preferable that the connecting spaces between the sample inlet ports and the sample ejection ports in the pipette main body can be cleaned, so that a greater number of various kind DNA fragments or the like can be ejected into micro spots, preserving a clean state without any pollution. Furthermore, the supply of the respective samples into the corresponding sample inlet ports can be carried out by opening the bottom of the cartridge with needles or the like after the cartridge is set at a position of the sample inlet ports. Otherwise, it can be achieved if needles or the like are disposed in the vicinity of the sample inlet ports in advance, and the opening of the bottoms with the needles can be simultaneously made in conjunction with the setting of the cartridge. Furthermore, a mechanism for supplying gas after opening can be added to the above system in order to compel to push out the samples.

III. Method for Producing Biochips

Novelty in the method for producing biochips such as DNA micro arrays according to the invention resides in using the above-mentioned dispenser.

Generally, a sample containing DNA fragments spotted as DNA micro arrays is used, amplifying the DNA fragments in the first cartridge 60 in FIG. 17. In the case of using a dispenser in which micropipettes according to the invention are used, the amplification can be carried out in the micropipettes, since the micropipettes in the pipette main body have a space to some extent.

When the method for producing a biochip according to the invention is applied to the preparation of DNA micro arrays, the following steps are carried out:

In the case of using DNA fragments, amplifying them in the first cartridge 60, the cartridge filled with a buffer solution as a substitution solution is prepared in advance, and then the buffer solution is transferred into a cavity of each micropipette. Subsequently, a cartridge containing a sample of DNA fragments is set so as to face the sample inlet ports, and then the sample is supplied into the sample inlet ports by breaking the bottom of the cartridge with needles or the like. After that, by activating the piezoelectric/ electrostrictive elements, the buffer solution stored in advance is discharged from the sample ejection ports and the buffer solution in the cavities is substituted with the sample.

The end point of substitution can be determined, based on the volume of the buffer solution discharged. However, it can be preferably determined by the action of the piezoelectric/electrostrictive elements, which are used as a sensor for sensing the viscosity and the specific gravity of the liquid in the cavities with the aid of relay switching. After the end of substitution, the piezoelectric/ electrostrictive elements are activated under the driving conditions determined by the amount of a droplet, which corresponds to the spot size to be obtained, and thus the DNA micro arrays are produced by repeating the spotting procedure. Normally, a spot is produced by one to several hundred droplets ejected from a micropipette. When the sample in the sample inlet ports is decreased, the buffer solution is added thereto, and the eject is continued, preventing bubbles from intruding into the fluid channels. Hence, the sample can be completely used without leaving it in the micropipettes. The end of substituting the sample with the substitution solution (the end of ejecting the sample) is similarly determined by sensing the viscosity and specific gravity of the liquid with the piezoelectric/ electrostrictive elements. In another way, the spots can be produced by dropping an initial dilute sample solution onto a substrate, and then by evaporating the solvent. This method ensures to reduce the amount of sample left in the fluid channels, thereby enabling the efficiency in the usage of the sample to be enhanced.

Moreover, it is preferable that the substitution solution and the sample, from which a gas is removed in advance with a degassing treatment, are used. Such a solution ensures to avoid the failures resulting from the bubbles left in the fluid channels and the incomplete charge of the solution, when the fluid channels are filled with the solution, because the bubbles can be dissolved into the solution. Moreover, such a solution suppresses the failures in the ejecting process, which result form the generation of bubbles in the fluid channels.

EXAMPLES

In the following, the present invention will be further described, based on several embodiments. However, it should be noted that these embodiments provide no limitations to the invention.

In the embodiment shown in FIG. 4, a through hole was machined with an exicmer laser in a PET resin sheet having a thickness of 38 µm as a nozzle element. The profile of the through hole was machined, using the so-called mask method in which a mask having a shape of the profile similar to the cross section of the through hole was positioned in the ray path of laser beam illumination. The illumination of the laser beam was carried out from the sample supplying opening end 23 to the sample discharging opening end 24 of the through hole, and the mask for the through hole, whose shape at the sample supplying opening end 23 is shown in FIG. 3A, was designed in such a manner that the diameter L4 of the inscribed circle for the projections was 75 µm, the angle θ between straight lines connecting the origin to the respective adjacent projections was 15 degrees, and the line length L3 of the projection 8 was 13 µm. The section of the throughhole being parallel to its axial direction was machined with the mask method by appropriately adjusting the power of the laser so as to make the section have a tapered shape toward the sample discharging opening end. The power of the laser was set at a smaller value, compared with the value (30 mJ/sec) at which the through hole could be machined within several seconds, so that the machining was completed after using a relative long period machining time. In an actual case, the tapered shape was machined for 20 sec by adjusting the power of the laser at 20 mJ/sec. In this case, the shape of the through hole at the sample discharging opening end 24 in FIG. 3A was machined such that the diameter L4 of the inscribed circle for the projections was 50 µm, the angle θ between straight lines connecting the origin to the respective adjacent projections was 15 degrees, and the line length L3 of the projection 8 was 8 µm.

In the embodiment shown in FIG. 6, the through hole was machined with a similar mask method using a mask having a shape of the a circle profile which is similar to the cross section of the through hole at the sample supplying opening end 23. In this case, the power of the laser was set in each step at a value smaller than that in the above conditions, and the through hole, whose profile was approximately circular at the sample supplying opening end 23 and has projections at the sample discharging opening end 24, was machined. In an actual case, the through hole was machined under conditions of laser power of 10 mJ and an illumination period of 20 sec, such that the through hole at the sample supplying opening end 23 was a circle having a diameter of 80 µm and at the sample discharging opening end 24, as shown in FIG. 3A, the diameter L4 of the inscribed circle for the projections was 50 µm, the angle θ between straight lines connecting the origin to the respective adjacent projections was 15 degrees, and the line length L3 of the projection 8 was 8 µm.

Using a micropipette having the through holes which are shown either in FIG. 4 or in FIG. 6, a sample in which DNA fragments having a base pair length of 1000 bp ware dissolved in a ×1 TE buffer (buffer solution) in a concentration of 1 µg/µl was repeatedly discharged. In this case, the so-called satellites were no longer generated even if the ejecting was repeated 100,000 times. Moreover, no failure in ejecting due to sample being dried near nozzles occurred in the course of ejecting process and a good performance for ejecting could be obtained, even if the period of ejecting was increased more than 10 sec.

In order to avoid the generation of splashes caused by a high energy of the droplets adhered to the slide substrate due to a high speed of ejecting, the displacement speed of the piezoelectric/electrostrictive elements was reduced, and therefore the ejecting speed of the droplets was also reduced. Even if the ejecting speed was set 1/2 times of the normally used speed (less than 4 m/sec), neither satellites were generated, nor the instability of ejecting, such as the deflection of the ejecting direction occurred.

What is claimed is:

1. A micropipette, comprising:
a pipette main body;
a sample inlet port through which a sample is supplied into said pipette main body;
a cavity in communication with said sample inlet port, into which the sample is received and temporarily stored;
a nozzle portion including a sample ejection port in communication with said cavity, said sample ejection port having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port, includes at least three projections extending radially away from said center axis, wherein each projection is defined by two adjacent surfaces that are either (1) linear and define at least one of at least one acute angle and at least one obtuse angle, or (2) curved, and wherein a cross-sectional area of said sample ejection port gradually decreases from said first end of said sample ejection port toward said second end of said sample ejection port; and
a piezoelectric/electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port.

2. A micropipette according to claim 1, wherein an angle between straight lines determined by connecting apexes of adjacent projections to said center axis of said sample ejection port is 1 degree to 120 degrees.

3. A micropipette according to claim 1, wherein a total length (L1) of the circumference of said cross-section of said ejection port including said at least three projections is more than 1.1 times larger than a length (L2) of the circumference of a circle having the same area as said cross-section of said ejection port.

4. A micropipette according to claim 1, wherein a rate of the gradual decrease in said cross-sectional area of said sample ejection port is continuous from said first end of said sample ejection port to a predetermined distance toward said second end of said sample ejection port, and is greater than a rate of continuous decrease in the cross-sectional area from said predetermined distance to said second end of said sample ejection port.

5. A micropipette according to claim 1, wherein a surface roughness of said inner surface of said sample ejection port is greater than a surface roughness of a surface of said cavity through which said first end of said sample ejection port is formed.

6. A micropipette according to claim 1, wherein said second end of said sample ejection port comprises a sample discharge opening and a surface proximate said second end of said sample ejection port is treated with a liquid repellent.

7. A micropipette according to claim 1, wherein at least a portion of said pipette main body where said cavity and said piezoelectric/electrostrictive element are disposed is formed from zirconia ceramics.

8. A micropipette according to claim 7, wherein said pipette main body formed from zirconia ceramics is produced by laminating and sintering green sheets.

9. A micropipette according to claim 1, wherein said pipette main body is formed from a resin at least at a portion where said sample ejection port is formed.

10. A micropipette according to claim 1, wherein said piezoelectric/electrostrictive element comprises piezoelectric/electrostrictive layers including at least one lead compound selected from the group consisting of lead zirconate, lead titanate and lead magnesium niobate as a main component.

11. A micropipette according to claim 1, wherein said pipette main body further comprises a plurality of sample inlet ports, a plurality of cavities and a plurality of sample ejection ports.

12. A micropipette according to claim 1, wherein said cavity and said piezoelectric/electrostrictive element are disposed in a first pipette unit, and a plurality of said sample inlet ports and a plurality of said sample ejection ports are disposed in a second pipette unit, and a plurality of said first and second pipette units are bonded to one another to form said pipette main body.

13. A micropipette according to claim 1, wherein said pipette main body comprises a flat plate including an upper surface, a lower surface and side surfaces, and said sample ejection port is disposed on one of said side surfaces, said upper surface and said lower surface.

14. A micropipette according to claim 1, wherein said pipette main body comprises a flat plate including an upper surface, a lower surface and side surfaces, said sample ejection port and said sample inlet port each being disposed on one of said upper, lower and side surfaces such that said sample ejection port and said sample inlet port are disposed on different surfaces of said pipette main body.

15. A micropipette according to claim 1, wherein a plurality of said sample inlet ports are in communication with said cavity.

16. A micropipette, comprising:
a pipette main body;
a sample inlet port through which a sample is supplied into said pipette main body,
a cavity in communication with said sample inlet port, into which the sample is received and temporarily stored;
a nozzle portion including a sample ejection port in communication with said cavity, said sample ejection port having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port, has an approximately circular shape which extends a first predetermined distance from said first end of said sample ejection port toward said second end of said sample ejection port, and another cross-section of said sample ejection port, when viewed in said plane, includes at least three projections extending radially away from said center axis, wherein each projection is defined by two adjacent surfaces that are either (1) linear and define at least one of at least one acute angle and at least one obtuse angle, or (2) curved, said projections extending from said first predetermined distance toward said second end of said sample ejection port, and wherein a cross-sectional area of said sample ejection port gradually decreases from said first end of said sample ejection port toward said second end of said sample ejection port; and a piezoelectric/electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port.

17. A micropipette composite unit, comprising:
a plurality of micropipettes bonded to one another and selected from the group consisting of micropipettes (i) and (ii), wherein
micropipette (i) comprises a pipette main body comprising (a) a sample inlet port through which a sample is supplied into said pipette main body, (b) a cavity in communication with said sample inlet port, into which the sample is received and temporarily stored, (c) a nozzle portion including a sample ejection port in communication with said cavity, the sample ejection port having an inner surface and first and second ends opposite to one another, said sample being discharged from said cavity and out of said pipette main body through said sample ejection port, wherein a cross-section of said sample ejection port, when viewed in a plane perpendicular to a center axis of said sample ejection port, includes at least three projections extending radially away from said center axis, wherein each projection is defined by two adjacent surfaces that are either (1) linear and define at least one of at least one acute angle and at least one obtuse angle, or (2) curved, and wherein a cross-sectional area of said sample ejection port gradually decreases from said first end of said sample ejection port toward said second end of said sample ejection port, and (d) a piezoelectric/electrostrictive element mounted on an outer surface of said pipette main body above said cavity, the activation of said piezoelectric/electrostrictive element changing the volume of said cavity to cause a predetermined amount of the sample stored in said cavity to be discharged from said sample ejection port, and
micropipette (ii) comprises a pipette main body including (a) a sample inlet port through which a sample is supplied into said pipette main body, (b) a cavity in communication with said sample inlet port, into which the sample is received and temporarily stored, (c) a nozzle portion including a sample ejection port in communication with said cavity, said sample ejection port having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port has an approximately circular shape extending a first predetermined distance from said first end of said sample ejection port toward said second end of said sample ejection port, and another cross-section of said sample ejection port, when viewed in said plane, includes at least three projections extending radially away from said center axis, wherein each projection is defined by two adjacent surfaces that are either (1) linear and define at least one of at least one acute angle and at least one obtuse angle, or (2) curved, said projections extending from said first predetermined distance toward said second end of said sample ejection port, and wherein a cross-sectional area of said sample ejection port gradually decreases from said first end of said sample ejection port toward said second end of said sample ejection port, and (d) a piezoelectric/electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port.

18. A dispenser, comprising:

an array of micropipette composite units each comprising a plurality of micropipettes bonded to one another, said array of micropipette composite units including sample ejection ports disposed in the form of a matrix, with the same or different types of liquid samples being ejected from said sample ejection ports, and said micropipettes in said micropipette composite units being selected from the group consisting of micropipettes (i) and (ii), wherein micropipette (i) comprises a pipette main body comprising (a) a sample inlet port through which a sample is supplied into said pipette main body, (b) a cavity in communication with said sample inlet port, into which the sample is received and temporarily stored, (c) a nozzle portion including a sample ejection port in communication with said cavity, said sample ejection port having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port, includes at least three projections extending radially away from said center axis, wherein each projection is defined by two adjacent surfaces that are either (1) linear and define at least one of at least one acute angle and at least one obtuse angle, or (2) curved, and wherein a cross-sectional area of said sample ejection port gradually decreases from said first end of said sample ejection port toward said second end of said sample ejection port, and (d) a piezoelectric/electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port, and micropipette (ii) comprises a pipette main body including (a) a sample inlet port through which a sample is supplied into said pipette main body, (b) a cavity in communication with said sample inlet port, into which the sample is received and temporarily stored, (c) a nozzle portion including a sample ejection port in communication with said cavity and having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port, has an approximately circular shape extending a first predetermined distance from said first end of said sample ejection port toward said second end of said sample ejection port, and another cross-section of said sample ejection port, when viewed in said plane, includes at least three projections extending radially away from said center axis, wherein each projection is defined by two adjacent surfaces that are either (1) linear and define at least one of at least one acute angle and at least one obtuse angle, or (2) curved, said projections extending from said first predetermined distance toward said second end of said sample ejection port, and wherein a cross-sectional area of said sample ejection port gradually decreases from said first end of said sample ejection port toward said second end of said sample ejection port, and (d) a piezoelectric/electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port.

19. A dispenser according to claim 18, further comprising a first cartridge including liquid samples stored therein, said first cartridge being disposed to face said sample inlet ports.

20. A dispenser according to claim 18, further comprising a second cartridge including one of an aqueous solvent and an organic solvent stored therein, and being disposed to face said sample inlet ports, wherein connecting spaces formed from said sample inlet ports to said sample ejection ports are cleaned with said one of said aqueous solvent and said organic solvent.

21. A dispenser according to claim 18, further comprising a thin plate for rejecting droplets flying in a deviated direction is disposed to face the said sample ejection ports in said pipette main body, said thin plate having openings with centers coaxially aligned in a direction of the center axes of said sample ejection ports.

22. A method of producing a biochip, comprising:

providing a micropipette comprising (a) a pipette main body, (b) a sample inlet port through which a sample is supplied into said pipette main body, (c) a cavity in communication with said sample inlet port, into which the sample is received and temporarily stored, (d) a nozzle portion including a sample ejection port in communication with said cavity, said sample ejection port having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port, includes at least three projections extending radially away from said center axis, wherein each projection is defined by two adjacent surfaces that are either (1) linear and define at least one of at least one acute angle and at least one obtuse angle, or (2) curved, and wherein a cross-sectional area of said sample ejection port gradually decreases from said first end of said sample ejection port toward said second end of said sample ejection port, and (e) a piezoelectric/ electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port; and ejecting a sample solution from said micropipette to form said biochip comprising at least one sample spot on a base plate.

23. A method of producing a biochip, comprising:

providing a micropipette comprising (a) a pipette main body, (b) a sample inlet port through which a sample is supplied into said pipette main body, (c) a cavity in communication with said sample inlet port, into which the sample is received and temporarily stored, (d) a nozzle portion including a sample ejection port in communication with said cavity, said sample ejection port having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port, has an approximately circular shape which extends a first predetermined distance from said first end of said sample ejection port toward said second end of said sample ejection port, and another cross-section of said sample ejection port, when viewed in said plane, includes at least three projections extending radially away from said center axis, wherein each projection is defined by two adjacent surfaces that are either (1) linear and define at least one of at least one acute angle and at least one obtuse angle, or (2) curved, said projections extending from said first predetermined distance toward said second end of said sample ejection port, and wherein a cross-sectional area of said sample ejection port gradually decreases from said first end of said sample ejection port toward said second end of said sample ejection port, and (e) a piezoelectric/electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port; and ejecting a sample solution from said micropipette to form said biochip comprising at least one sample spot on a base plate.

24. A method of producing a biochip, comprising:

providing a micropipette composite unit comprising a plurality of micropipettes bonded to one another and selected from the group consisting of micropipettes (i) and (ii), wherein micropipette (i) comprises a pipette main body comprising (a) a sample inlet port through which a sample is supplied into said pipette main body, (b) a cavity in communication with said sample inlet port, into which the sample is received and temporarily stored, (c) a nozzle portion including a sample ejection port in communication with said cavity, said sample ejection port having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port, includes at least three projections extending radially away from said center axis, wherein each projection is defined by two adjacent surfaces that are either (1) linear and define at least one of at least one acute angle and at least one obtuse angle, or (2) curved, and wherein a cross-sectional area of said sample ejection port gradually decreases from said first end of said sample ejection port toward said second end of said sample ejection port, and (d) a piezoelectric/electrostrictive element mounted on an outer surface of said pipette main body above said cavity, the activation of said piezoelectric/electrostrictive element changing the volume of said cavity to cause a predetermined amount of the sample stored in said cavity to be discharged from said sample ejection port, and micropipette (ii) comprises a pipette main body including (a) a sample inlet port through which a sample is supplied into said pipette main body, (b) a cavity in communication with said sample inlet port, into which the sample is received and temporarily stored, (c) a nozzle portion including a sample ejection port in communication with said cavity, said sample ejection port having an inner surface and first and second ends opposite to one another, the sample being discharged from said cavity and out of said pipette main body through said sample ejection port, wherein a cross-section of said sample ejection port, when viewed in said plane perpendicular to a center axis of said sample ejection port, has an approximately circular shape extending a first predetermined distance from said first end of said sample ejection port toward said second end of said sample ejection port, and another cross-section of said sample ejection port, when viewed in said plane, includes at least three projections extending radially away from said center axis, wherein each projection is defined by two adjacent surfaces that are either (1) linear and define at least one of at least one acute angle and at least one obtuse angle, or (2) curved, said projections extending from said first predetermined distance toward said second end of said sample ejection port, and wherein a cross-sectional area of said sample ejection port gradually decreases from said first end of said sample ejection port toward said second end of said sample ejection port, and (d) a piezoelectric/electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port; and ejecting a sample solution from said micropipette to form said biochip comprising at least one sample spot on a base plate.

25. A method of producing a biochip, comprising:

providing a dispenser comprising an array of micropipette composite units each comprising a plurality of micropipettes bonded to one another, said array of micropipette composite units including sample ejection ports disposed in the form of a matrix, with the same or different types of liquid samples being ejected from said sample ejection ports, and said micropipettes in said micropipette composite units being selected from the group consisting of micropipettes (i) and (ii), wherein micropipette (i) comprises a pipette main body comprising (a) a sample inlet port through which a sample is supplied into said pipette main body, (b) a cavity in communication with said sample inlet port, into which the sample is received and temporarily stored, (c) a nozzle portion including a sample ejection port in communication with said cavity, said sample ejection port having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port, includes at least three projections extending radially away from said center axis, wherein each projection is defined by two adjacent surfaces that are either (1) linear and define at least one of at least one acute angle and at least one obtuse angle, or (2) curved, and wherein a cross-sectional area of said sample ejection port gradually decreases from said first end of said sample ejection port toward said second end of said sample ejection port, and (d) a piezoelectric/electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port, and micropipette (ii) comprises a pipette main body including (a) a sample inlet port through which a sample is supplied into said pipette main body, (b) a cavity in communication with said sample inlet port, into which the sample is received and temporarily stored, (c) a nozzle portion including a sample ejection port in communication with said cavity and having an inner surface and first and second ends opposite to one another, the sample being discharged from said cavity and out of said pipette main body through said sample ejection port, wherein a cross-section of said sample ejection port, when viewed in a plane perpendicular to a center axis of said sample ejection port has an approximately circular shape extending a first predetermined distance from said first end of said sample ejection port toward said second end of said sample ejection port, and another cross-section of said sample ejection port, when viewed in said plane, includes at least three projections extending radially away from said center axis, wherein each projection is defined by two adjacent surfaces that are either (1) linear and define at least one of at least one acute angle and at least one obtuse angle, or (2) curved, said projections extending from said first predetermined distance toward said second end of said sample ejection port, and wherein a cross-sectional area of said sample ejection port gradually decreases from said first end of said sample ejection port toward said second end of said sample ejection port, and (d) a piezoelectric/electrostrictive element mounted on an outer surface of said pipette main body above said cavity, the activation of said piezoelectric/electrostrictive element changing the volume of said cavity to cause a predetermined amount of the sample stored in said cavity to be ejected from said sample ejection port; and ejecting a sample solution from said micropipette to form said biochip comprising at least one sample spot on a base plate.

* * * * *